(12) United States Patent
Dupree

(10) Patent No.: US 8,187,238 B1
(45) Date of Patent: May 29, 2012

(54) MALE INCONTINENCE GARMENT

(76) Inventor: Charles B. Dupree, Singer Island, FL (US)

( * ) Notice: Subject to any disclaimer, the term of this patent is extended or adjusted under 35 U.S.C. 154(b) by 0 days.

(21) Appl. No.: 12/888,515

(22) Filed: Sep. 23, 2010

(51) Int. Cl.
*A61F 5/44* (2006.01)

(52) U.S. Cl. ........ 604/349; 604/347; 604/351; 604/352; 604/353

(58) Field of Classification Search .......... 604/349, 604/347, 351, 352, 353
See application file for complete search history.

(56) References Cited

U.S. PATENT DOCUMENTS

| | | | |
|---|---|---|---|
| 3,863,638 A * | 2/1975 | Rogers et al. ............... 604/352 |
| 4,568,340 A * | 2/1986 | Giacalone .................... 604/353 |
| 4,731,070 A | 3/1988 | Koci |
| 4,769,020 A * | 9/1988 | Eaton ........................... 604/352 |
| 4,790,834 A * | 12/1988 | Austin ......................... 604/349 |
| 5,275,592 A | 1/1994 | Grizzaffi |
| 5,618,277 A | 4/1997 | Goulter |
| 5,618,279 A | 4/1997 | Pudlo |
| 5,662,630 A * | 9/1997 | Raynie .......................... 604/349 |
| 5,695,485 A | 12/1997 | Duperret et al. |
| 5,797,890 A * | 8/1998 | Goulter et al. ................ 604/351 |
| 6,209,543 B1 * | 4/2001 | Star .............................. 128/844 |
| 6,443,930 B1 | 9/2002 | Silverstein |
| 6,569,135 B1 | 5/2003 | Mula |
| 2007/0043329 A1 | 2/2007 | Evans |
| 2007/0073252 A1 * | 3/2007 | Forgrave ....................... 604/349 |
| 2008/0243097 A1 * | 10/2008 | Goss ............................. 604/349 |
| 2009/0270822 A1 * | 10/2009 | Medeiros ...................... 604/347 |

* cited by examiner

*Primary Examiner* — Tatyana Zalukaeva
*Assistant Examiner* — Ginger T Chapman
(74) *Attorney, Agent, or Firm* — Montgomery Patent & Design, LLC; Robert C. Montgomery; Joseph T. Yaksich

(57) ABSTRACT

A urine collection device for males suffering from incontinence comprises a collection bag worn under an inner garment. The collection bag is sized to receive the entire content of a full bladder. The open end of an integral input sleeve comprises an elastic band and hook-and-loop closure members as a means of ensuring a comfortable fit, a tight seal, and a secure retention of the device. The internal portion of the collection bag comprises absorbent, jellying, and disinfecting materials. An adhesive strip provides a means of removably attaching the collection bag onto the inside of an inner garment. The device is disposable, made of flexible bio-degradable material and is intended to be removed and discarded after each use.

5 Claims, 6 Drawing Sheets

MALE INCONTINENCE GARMENT

FIELD OF THE INVENTION

The present invention relates generally to protective undergarments, and in particular, to a garment adapted for protection of males suffering from incontinence.

BACKGROUND OF THE INVENTION

Urinary incontinence is a common condition resulting from a number of different causes. This condition is seen as highly distressing due to the fact that such accidents, when occurring in the presence of others, can lead to high levels of embarrassment by the afflicted. Due to the uncontrollable nature of this condition, constant precautions must be taken in order to prevent accidental mishaps at inopportune times.

While such mishaps are viewed as highly embarrassing, many conventional protective measures can lead to embarrassment in and of themselves. For instance, absorbent incontinence pads are often bulky and can be clearly seen in outline form under one's clothes. Additionally, they are uncomfortable and hot to wear, especially in warm weather. In general, the amount of protection provided is proportional to the discomfort and visibility of the protecting device.

Various attempts have been made to provide protective devices adapted for males with urinary incontinence. Examples of these attempts can be seen by reference to several U.S. patents. U.S. Pat. No. 4,731,070, issued in the name of Koci, describes an absorbent article with formed with an absorbent batt portion and corresponding moisture impervious sheets.

U.S. Pat. No. 5,275,592, issued in the name of Grizzaffi, describes an apparatus for incontinent males with a pocket and disposable inserts supported by a waist band portion.

U.S. Pat. No. 5,695,485, issued in the name of Duperret et al., describes a male continence pouch and shield to accommodate small and large incidents of incontinence.

While these devices fulfill their respective, particular objectives, each of these references suffer from one (1) or more of the aforementioned disadvantages. Many such devices do not provide a sufficient level of protection, particularly for significant incidents of incontinence. Also, many such devices do not adequately protect a user's penis in order to prevent discomfort after an incontinence incident. Furthermore, many such devices are readily apparent even when covered with normal clothing, contributing to embarrassment on the part of a user. Accordingly, there exists a need for a male incontinence garment without the disadvantages as described above. The development of the present invention substantially departs from the conventional solutions and in doing so fulfills this need.

SUMMARY OF THE INVENTION

In view of the foregoing references, the inventor recognized the aforementioned inherent problems and observed that there is a need for a garment which protects a user from small and large incontinence incidents in a manner which is comfortable and discreet. Thus, the object of the present invention is to solve the aforementioned disadvantages and provide for this need.

To achieve the above objectives, it is an object of the present invention to provide a means for preventing accidents and discomfort for males suffering from urinary incontinence. The device comprises a collector bag, a sleeve, and a closure.

Another object of the present invention is to provide a means for use with an existing undergarment and outer garment. The collector bag is removably fastenable to an undergarment via an integral adhesive strip.

Yet still another object of the present invention is to provide a means for the retention of urine leaked during an incontinence incident. The sleeve portion of the device is adapted to comfortably engage a user's penis. The urine is collected in the bag portion which is integrally attached to the sleeve.

Yet still another object of the present invention is to comprise the interior surface of the sleeve of a semi-absorbent lining which provides a barrier between a user's penis and the plastic exterior of the device. The lining further provides padding and sealing functions to the device.

Yet still another object of the present invention is to provide a means of disinfecting and jellying trap urine within the collector bag. The device further comprises a deodorizing liner and polymer absorbent packet within the collector bag.

Yet still another object of the present invention is to facilitate disposal of the device via constructing the collector bag and sleeve of a flexible bio-degradable plastic material.

Yet still another object of the present invention is to provide a means of size adjustment of the inner portion of the sleeve via the closure, in order to facilitate secure placement of the device while allowing a user to selectively adjust the tightness of the sleeve. The closure comprises an elastic band and a pair of adjustable straps.

Yet still another object of the present invention is to provide a method of utilizing the device that provides a unique means of obtaining an instance of the device of a desired size, inserting the penis into the sleeve, selectively adjusting the tightness of the sleeve via the closure, securing the device in place via the adhesive portion and straps, collecting leaked urine in the collector bag, jelling and deodorizing collected urine via the polymer packet and liner, removing the collector bag after use, and discarding the used device.

Further objects and advantages of the present invention will become apparent from a consideration of the drawings and ensuing description.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTIVE KEY

| | |
|---|---|
| 10 | male incontinence garment |
| 11 | collector bag |
| 12 | sleeve |
| 13 | elastic band |
| 14 | first strap |
| 15 | second strap |
| 16 | connection member |
| 17 | adhesive strip |
| 18 | adhesive backing |
| 21 | sleeve lining |
| 22 | deodorizing liner |
| 23 | absorbent packet |
| 24 | additional liner |
| 60 | user |
| 61 | outer garment |
| 62 | inner garment |

DETAILED DESCRIPTION OF THE PREFERRED EMBODIMENT

Figure 1:
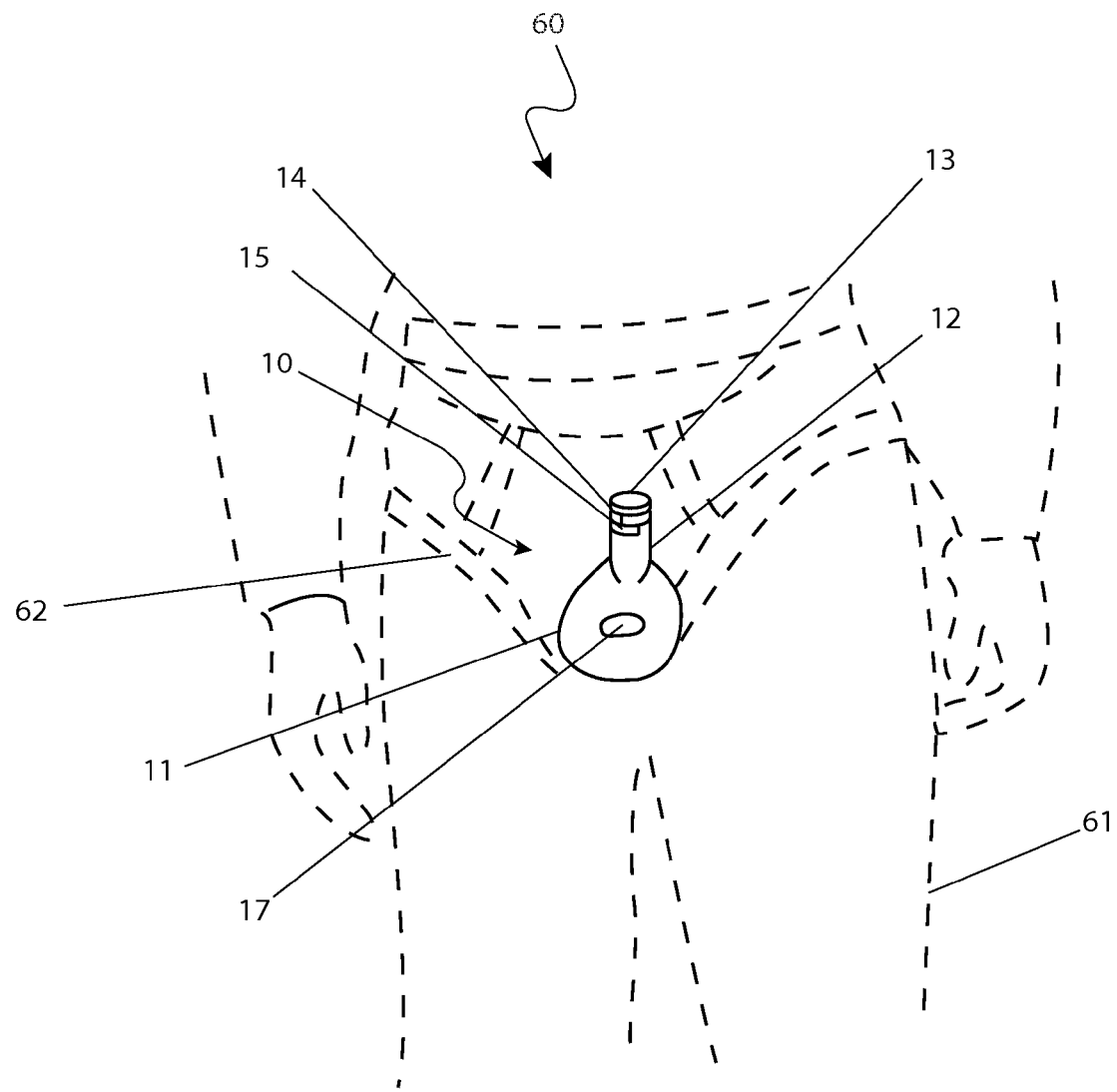
FIG. 1 is an environmental view of a male incontinence garment 10, according to a preferred embodiment of the present invention.
Figure 2A:
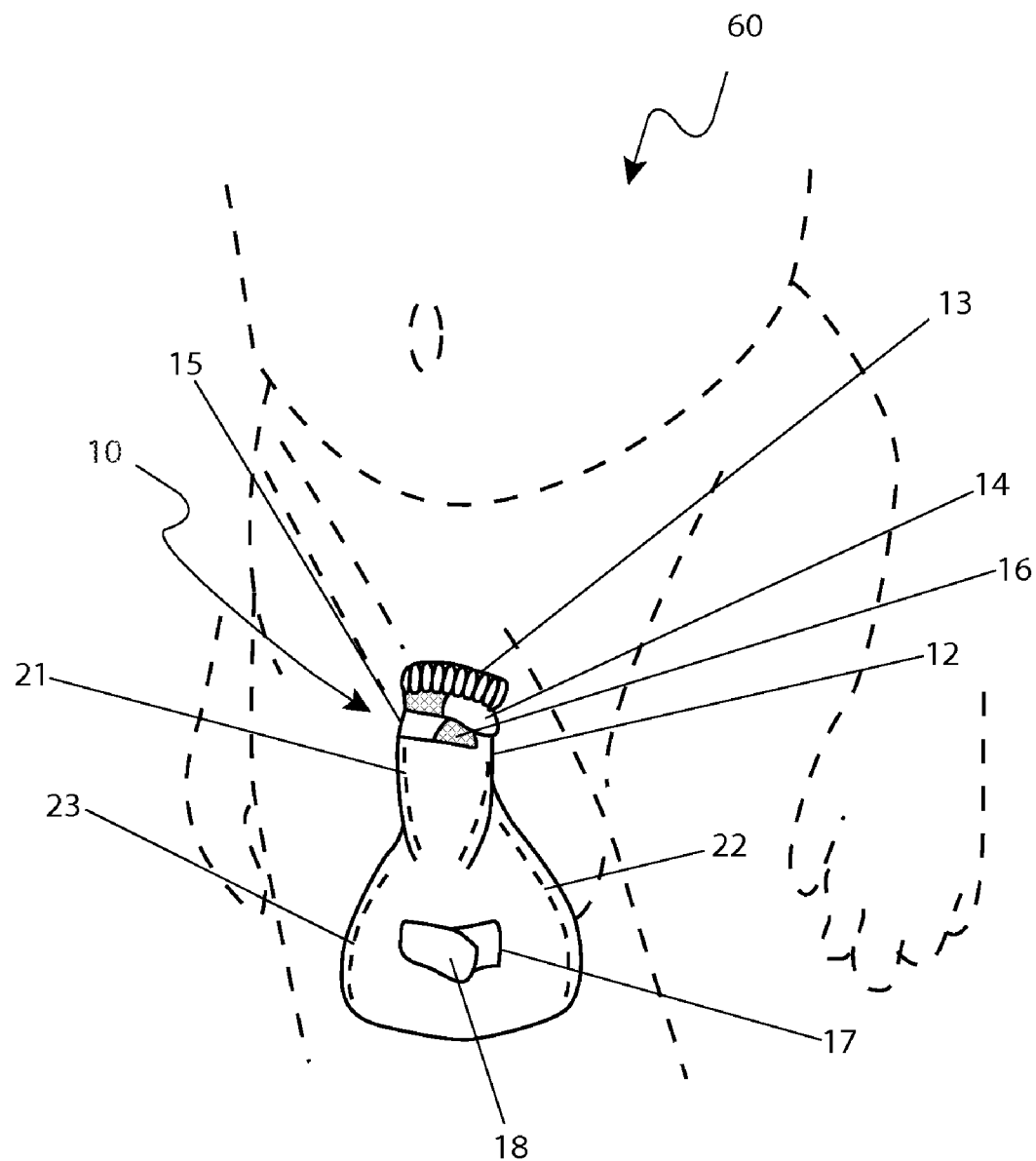
FIG. 2a is a perspective view of the male incontinence garment 10 in an initially installed state, according to the preferred embodiment of the present invention.
Figure 2B:
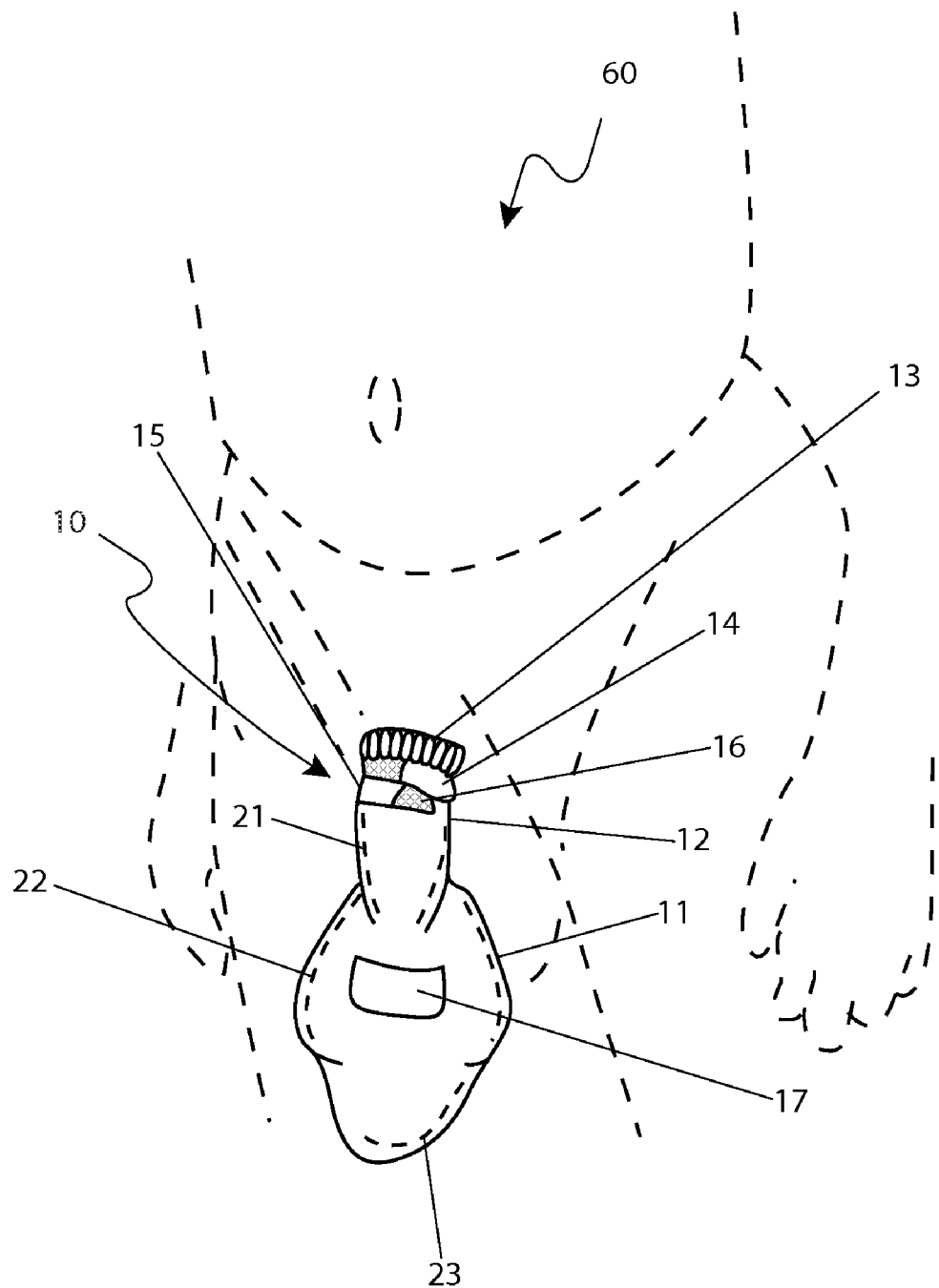
FIG. 2b is a perspective view of the male incontinence garment 10 in a filled state, according to the preferred embodiment of the present invention.
Figure 2C:
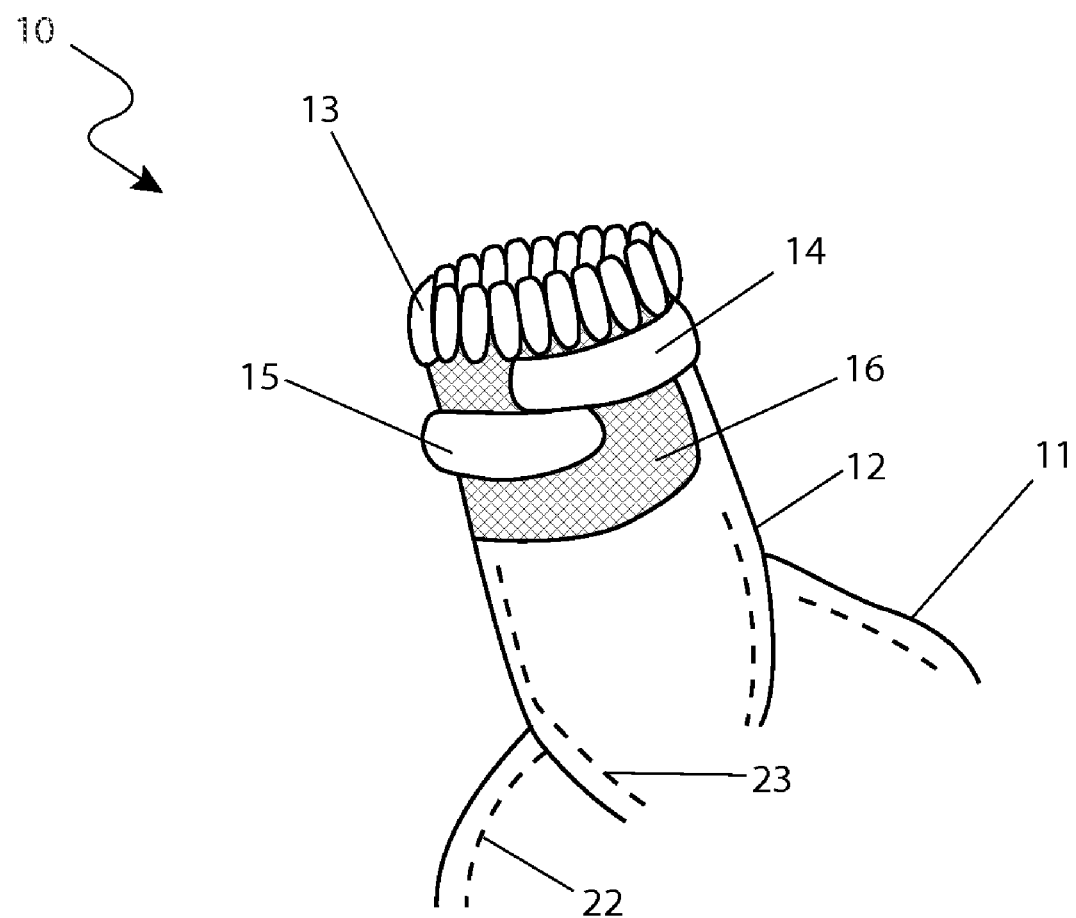
FIG. 2c is a perspective enlarged view of a sleeve 12 of the male incontinence garment 10, according to the preferred embodiment of the present invention.
Figure 2D:
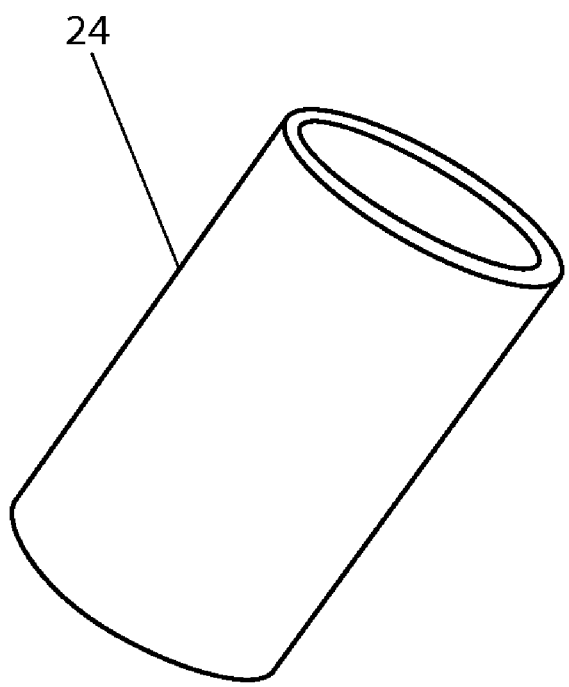
FIG. 2d is a perspective view of an additional liner 24 for the male incontinence garment 40, according to an alternate embodiment of the present invention; and, FIG. 2e is a partially cut-away perspective view of the sleeve 12 of the male incontinence garment 40, according to the preferred embodiment of the present invention.
Figure 2E:
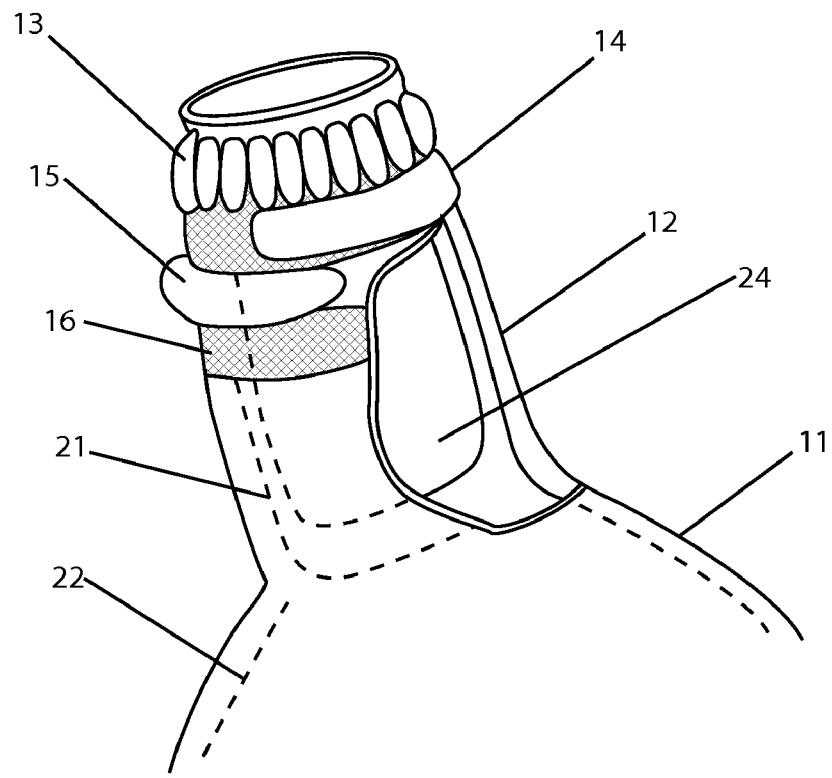

The best mode for carrying out the invention is presented in terms of its preferred embodiment, herein depicted within FIGS. 1 through 2e. However, the invention is not limited to the described embodiment and a person skilled in the art will appreciate that many other embodiments of the invention are possible without deviating from the basic concept of the invention, and that any such work around will also fall under scope of this invention. It is envisioned that other styles and configurations of the present invention can be easily incorporated into the teachings of the present invention, and only one particular configuration shall be shown and described for purposes of clarity and disclosure and not by way of limitation of scope.

The terms "a" and "an" herein do not denote a limitation of quantity, but rather denote the presence of at least one of the referenced items.

The present invention describes a device and method for a male incontinence garment (herein described as the "device") 10, which provides a means for preventing discomfort, accidents, and embarrassment for males 60 suffering from incontinence.

Referring now to FIG. 1, an environmental view of the device 10, according to the preferred embodiment of the present invention, is disclosed. The device 10 is depicted as worn by a user 60 within an inner garment 62 and an outer garment 61. The device 10 comprises a collector bag 11, an integral sleeve 12 and a closure comprising an elastic band 13, a first strap 14 and a second strap 15. The inner garment 62 is envisioned to comprise either underwear or an athletic supporter.

Referring now to FIG. 2a, a perspective view of the device 10, according to the preferred embodiment of the present invention, is disclosed. The device 10 is depicted in a state of having been initially installed by the user 60, comprising the collector bag 11 and the sleeve 12. The upper portion of the sleeve 12 comprises the elastic band 13 and a hook-and-loop closure comprising a first strap 14, a second strap 15 and a connection member 16 designed to retain the first strap 14 and the opposing second strap 15 side by side. The front outer portion of the collector bag comprises an integral adhesive strip 17 which provides a means of removably fastening the collector bag 11 onto an inner portion of the inner garment 62 after the user 60 has exposed the adhesive strip 17 by peeling off the adhesive backing 18. The collector bag 11 and the integral sleeve 17 are envisioned to be made of a suitable flexible bio-degradable plastic material. The watertight integral configuration of the collector bag 11 and the sleeve 12 is envisioned to be produced by processes such as, but not limited to: heat sealing, welding, chemical bonding or blow-molding. The inner portion of the sleeve 12 comprises a lining 21 made of a gauze-like material to provide additional comfort in sealing and retaining the device 10 while eliminating the risk of an allergic reaction form the plastic material.

Referring now to FIG. 2b, a perspective view of the device 10, according to the preferred embodiment of the present invention, is disclosed. The device 10 is depicted in a state containing a full bladder content comprising approximately twenty-five (25) fluid ounces of urine. The inner portion of the collector bag 11 comprises a deodorizing liner 22. A polymer absorbent packet 23 is placed within the inner bottom portion of the collector bag 11 within the manufacturing process of the device 10 to provide a means of disinfecting and jellying the urine.

Referring now to FIG. 2c, a perspective enlarged view of the sleeve 12 of the device 10, according to the preferred embodiment of the present invention, is disclosed. The sleeve 12 comprises the elastic band 13, the first strap 14, the opposing second strap 15 and the connection member 16, all of which are integral members of the sleeve 12, attached onto by welding, heat sealing or chemical bonding. The rearward facing portion of each strap 14 and 15 comprises a first fastening element and the connection member 16 comprises a second fastening element, preferably of a hook-and-loop-type closure.

Referring now to FIG. 2d, a perspective view of a disposable additional liner 24 for the device 10, according to the preferred embodiment of the present invention, is disclosed. The additional liner 24 is envisioned to be made of a soft elastic medical grade plastic material and is intended to provide a means of additional size adjustment of the inner portion of the sleeve 12.

Referring now to FIG. 2e, a partially cut-away perspective view of the sleeve 12 comprising the additional liner 24 for the device 10, according to the preferred embodiment of the present invention, is disclosed. It is envisioned that additional liners 24 could be manufactured to comprise a plurality of internal sizes to provide the user 60 with an optimally comfortable and leak tight fit.

It is envisioned that other styles and configurations of the present invention can be easily incorporated into the teachings of the present invention, and only one particular configuration shall be shown and described for purposes of clarity and disclosure and not by way of limitation of scope.

The preferred embodiment of the present invention can be utilized by the common user in a simple and effortless manner with little or no training. After initial purchase or acquisition of the device 10, it would be installed as indicated in FIG. 1.

The method of utilizing the device 10 may be achieved by performing the following steps: cleaning and drying all skin areas of the user 60 contacted by the device 10; spreading the elastic band 13; inserting the entire length of a penis hereinto the sleeve 12; wrapping the first strap 14 around the sleeve 12; fastening the first strap 12 onto the upper portion of the connection member 16; adjusting the fit of the sleeve 12 by wrapping the second strap 15 around the sleeve 12 in a direction opposite of the first strap 14; fastening the second strap 15 onto a lower portion of the connection member 16 along the lower edge portion of the first strap 14; installing the inner garment 62; exposing the adhesive of the adhesive strip 17 by peeling off the adhesive backing 18; attaching collector bag 11 onto the inner garment 62 by pressing the front portion of the inner garment 62 against the adhesive strip 17; utilizing the device 10 by urinating into the collector bag 11, wherein the urine will be jelled by the polymer packet 23; separating the collector bag 11 from the inner garment 62 after urination; uninstalling the device 10 by following the installation steps in a reverse order without removing the inner garment 62 and the outer garment 61; discarding the used device 10; and, installing a fresh device 10 if needed.

An alternate method of utilizing the device 10 may be achieved by performing an additional step of inserting the additional liner 24 into the sleeve 12 if needed for a size adjustment; inserting the penis hereinto the additional liner 24; proceeding with the installation of the device 10 by following the similar to those described for regular device 10.

The foregoing descriptions of specific embodiments of the present invention have been presented for purposes of illustration and description. They are not intended to be exhaustive or to limit the invention and method of use to the precise forms disclosed. Obviously many modifications and variations are possible in light of the above teaching. The embodiment was chosen and described in order to best explain the principles of the invention and its practical application, and to thereby enable others skilled in the art to best utilize the invention and various embodiments with various modifications as are suited to the particular use contemplated. It is understood that various omissions or substitutions of equivalents are contemplated as circumstance may suggest or render expedient, but is intended to cover the application or implementation without departing from the spirit or scope of the claims of the present invention.

What is claimed is:

1. A male incontinence garment adapted to be worn by a male user for preventing discomfort, accidents, and embarrassment associated with incontinence, said male incontinence garment comprising:
    a collector bag having a sleeve, said sleeve adapted to be positioned about a penis of the male user such that said collector bag is adapted to receive urine from the penis of the male user; and,
    a polymer absorbent packet placed within said collector bag, said polymer absorbent packet adapted to disinfect and jellify the urine;
    wherein said sleeve comprises:
        a lining formed from gauze material and located at an inner portion of said sleeve;
        a disposable liner positioned inside said inner portion of said sleeve;
        an elastic band situated at an upper portion of said sleeve;
        first and second straps attached to said sleeve; and,
        a connection member attached to said sleeve;
        wherein said first and second straps are removably attached to said connection member for retaining said first strap adjacent to said second strap; and,
    wherein said collector bag and said sleeve are made of flexible bio-degradable plastic material.

2. The male incontinence garment of claim 1, wherein said collector bag comprises:
    a deodorizing liner located at an inner portion of said collector bag; and,
    an adhesive strip located at a front outer portion of said collector bag;
    wherein said adhesive strip is exposed by peeling off an adhesive backing from said adhesive strip and thereby adapting said collector bag to be removably fastened to an inner garment.

3. A male incontinence garment adapted to be worn by a male user for preventing discomfort, accidents, and embarrassment associated with incontinence, said male incontinence garment comprising:
    a collector bag having a sleeve, said sleeve adapted to be positioned about a penis of the male user such that said collector bag is adapted to receive urine from the penis of the male user; and,
    a polymer absorbent packet placed within an inner bottom portion of said collector bag, said polymer absorbent packet adapted to disinfect and jellify the urine;
    wherein said sleeve comprises:
        a lining formed from gauze material and located at an inner portion of said sleeve;
        a disposable liner positioned inside said inner portion of said sleeve;
        an elastic band situated at an upper portion of said sleeve;
        first and second straps attached to said sleeve; and,
        a connection member attached to said sleeve;
        wherein said first and second straps are removably attached to said connection member for retaining said first strap adjacent to said second strap; and,
    wherein said collector bag and said sleeve are made of flexible bio-degradable plastic material.

4. The male incontinence garment of claim 3, wherein said collector bag comprises:
    a deodorizing liner located at an inner portion of said collector bag; and,
    an adhesive strip located at a front outer portion of said collector bag;
    wherein said adhesive strip is exposed by peeling off an adhesive backing from said adhesive strip and thereby adapting said collector bag to be removably fastened to an inner garment.

5. A method of utilizing a male incontinence garment to be worn by a male user for preventing discomfort, accidents, and embarrassment associated with incontinence, said method comprising the steps of:
    providing a collector bag having a sleeve, said collector bag and said sleeve being made of flexible bio-degradable plastic material;
    wherein said sleeve comprises:
        a lining formed from gauze material and located at an inner portion of said sleeve;
        a disposable liner positioned inside said inner portion of said sleeve;
        an elastic band situated at an upper portion of said sleeve;
        first and second straps attached to said sleeve; and,
        a connection member attached to said sleeve;
        wherein said first and second straps are removably attached to said connection member for retaining said first strap adjacent to said second strap;
    providing and placing a polymer absorbent packet within an inner bottom portion of said collector bag;
    positioning said sleeve about a penis of the male user;
    said collector bag receiving urine from the penis of the male user; and,
    said polymer absorbent packet disinfecting and jellifying the urine.

* * * * *